(12) United States Patent
Tekulve et al.

(10) Patent No.: US 8,480,654 B2
(45) Date of Patent: Jul. 9, 2013

(54) CATHETER WITH EXPANDABLE FLOW AREA

(75) Inventors: Kurt John Tekulve, Ellettsville, IN (US); Michael Robert Kurrus, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/322,265

(22) PCT Filed: May 21, 2010

(86) PCT No.: PCT/US2010/035707
§ 371 (c)(1),
(2), (4) Date: Nov. 23, 2011

(87) PCT Pub. No.: WO2010/138398
PCT Pub. Date: Dec. 2, 2010

(65) Prior Publication Data
US 2012/0078186 A1      Mar. 29, 2012

Related U.S. Application Data

(60) Provisional application No. 61/180,984, filed on May 26, 2009.

(51) Int. Cl.
*A61M 25/00* (2006.01)
(52) U.S. Cl.
USPC .............. 604/528; 604/164.01; 604/164.13; 604/531
(58) Field of Classification Search
USPC ............ 604/93.01, 264, 158, 164.01, 164.13, 604/523, 528, 530, 531
See application file for complete search history.

(56) References Cited

U.S. PATENT DOCUMENTS

| | | | | |
|---|---|---|---|---|
| 4,411,655 A | * | 10/1983 | Schreck | 604/165.01 |
| 4,563,180 A | | 1/1986 | Jervis et al. | |
| 4,846,812 A | * | 7/1989 | Walker et al. | 604/264 |
| 5,011,488 A | * | 4/1991 | Ginsburg | 606/159 |
| 5,441,489 A | | 8/1995 | Utsumi et al. | |
| 5,976,120 A | * | 11/1999 | Chow et al. | 604/525 |

(Continued)

FOREIGN PATENT DOCUMENTS

| | | | |
|---|---|---|---|
| WO | WO 01/15763 | | 3/2001 |
| WO | WO 03/041782 | | 5/2003 |
| WO | WO2009/012492 | * | 1/2009 |
| WO | WO 2009/012492 | | 1/2009 |

*Primary Examiner* — Theodore Stigell
(74) *Attorney, Agent, or Firm* — Brinks Hofer Gilson & Lione (57) ABSTRACT

In at least one embodiment of the present invention, a catheter for insertion into a patient's body is provided. The catheter comprises an elongated member having a proximal portion extending to a distal portion. A lumen is formed through the proximal and distal portions. The elongated member is formed of a polymeric material including shape memory polymers having a first phase transition temperature and a second phase transition temperature that is less than the first phase transition temperature but is greater than about room temperature. The elongated member has a first configuration at about room temperature for insertion into the patient's body and self-configures to a second configuration at a first temperature of at least the second phase transition temperature for fluid communication with the patient's body. At least a portion of the lumen has a larger flow area in the second configuration than in the first configuration.

13 Claims, 6 Drawing Sheets

U.S. PATENT DOCUMENTS 6,183,443 B1 2/2001 Kratoska et al.
6,733,500 B2 * 5/2004 Kelley et al. .................... 606/41

2005/0004554 A1 1/2005 Osborne

* cited by examiner

CATHETER WITH EXPANDABLE FLOW AREA

CROSS REFERENCE TO RELATED APPLICATIONS

This application is related to and claims the benefit of priority to PCT/US2010/035707, filed on May 21, 2010 which application claims priority to and all available benefits of U.S. Provisional Patent Application No. 61/180,984, filed May 26, 2009, both of which are hereby incorporated by reference in their entirety.

BACKGROUND OF THE INVENTION

1. Field of the Invention

The present invention relates generally to catheters and more particularly, to a catheter having at least one lumen with an expandable flow area and a method for catheterizing a patient.

2. Background of the Invention

Catheters for the introduction or removal of fluids may be positioned in various venous locations and cavities throughout the body of a patient for introduction of fluids to the body or removal of fluids from the body. Such catheterizations may be performed using a catheter with either a single lumen or multiple lumens. Examples of such catheters are central venous catheters which are typically used for medical procedures such as blood pressure monitoring, blood sampling and the administration of drugs and fluids to a patient. These procedures often require that the catheter have a sufficiently sized lumen or lumens for administering fluids to the patient or withdrawal therefrom.

Generally, a central venous catheter is surgically inserted into a vein, such as the basilica, cephalic, subclavian, or jugular, with the distal tip of the catheter residing in the superior vena cava. These catheters are typically introduced using percutaneous entry techniques, such as the well-known Seldinger technique. In the Seldinger technique, the physician makes an oblique entry into the vein with a beveled needle. A wire guide is then inserted through the bore of the needle about 5 to 10 centimeters into the vein. The needle is thereafter withdrawn, leaving the wire guide in place. The catheter is then inserted over the wire guide, and advanced through the skin at the needle puncture site and into the vein. The Seldinger technique can be modified to include a peelable introducer which can be used to dilate the body vessel. In particular, the introducer sheath can be placed over the wire guide, and after removal of a dilator, the catheter can be placed through the sheath for insertion into the patient. In either of these procedures, the catheter is preferably sized such that the outer diameter (e.g. relatively small outer diameter) facilitates introduction of the catheter through the skin and into the vein. Once the catheter is in place within the vein, the wire guide is withdrawn and therapeutic treatment using the catheter can begin. Preferably, the catheter has sufficient flow area (e.g. catheter lumen with a relatively large flow area) for administering therapeutic treatment to the patient, such as for example, treating the patient with relatively large volumes of fluid during infusion therapy with a central venous catheter. When the therapeutic treatment is completed, the catheter is withdrawn from the patient. Preferably, the catheter is configured with an outer diameter (e.g. relatively small outer diameter) to facilitate being withdrawn from the patient. Currently available catheters with relatively large inner diameter lumens and currently available catheters with relatively small outer diameter shafts result in two diametrically opposed catheter constructions. That is, catheters with relatively large inner diameter lumens have corresponding relatively large outer diameter shafts and catheters with relatively small outer diameter shafts have corresponding relatively small inner diameter lumens.

Accordingly, it may be desirable to have a catheter with a relatively large flow area lumen for therapeutic treatment of a patient while having a relative small outer diameter for facilitating insertion into and/or withdrawal from the patient.

BRIEF SUMMARY OF THE INVENTION

In satisfying the above need and overcoming the above and other drawbacks and limitations of the known technology, the present invention provides a catheter for insertion into a patient's body. The catheter comprises an elongated member having a proximal portion extending to a distal portion. A lumen is formed through the proximal and distal portions. The elongated member is formed of a polymeric material including shape memory polymers having a first phase transition temperature. The shape memory polymers also have a second phase transition temperature that is less than the first phase transition temperature but is greater than about room temperature. The elongated member has a first configuration at about room temperature for insertion into the patient's body. At a first temperature of at least the second phase transition temperature, the elongated member self-configures to a second configuration for fluid communication with the patient's body. In the second configuration, at least a portion of the lumen has a larger flow area than in the first configuration.

In at least one other embodiment of the present invention, a catheterization kit is provided. The kit comprises the catheter as discussed in the foregoing paragraph and a wire guide for providing the catheter a path during insertion into the patient's body. A needle is provided for introducing the wire guide into the patient's body.

In one example, a method for catheterizing a patient's body for therapeutic treatment thereof is provided. The method comprises inserting an elongated member of a catheter into the patient's body. The elongated member is formed of a polymeric material including shape memory polymers having a first phase transition temperature and a second phase transition temperature that is less than the first phase transition temperature but is greater than about room temperature. At about room temperature, the elongated member is in a first configuration. The elongated member is heated to a first temperature of at least the second phase transition temperature where the elongated member self-configures to a second configuration. At least a portion of a lumen formed through the elongated member has a larger flow area in the second configuration than in the first configuration.

Further objects, features, and advantages of the invention will become apparent from consideration of the following description and the appended claims when taken in connection with the accompanied drawings.

DETAILED DESCRIPTION OF THE INVENTION

Detailed embodiments of the present invention are disclosed herein. It is understood however that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with inserting a catheter into and removing the catheter from a patient while providing a sufficiently sized lumen for providing therapeutic treatment to the patient. Preferably, the present invention provides a catheter, which is at least partially formed of shape memory polymers, and a method for using the catheter which facilitates inserting and/or removing the catheter while providing a sufficiently sized lumen for providing therapeutic treatment to the patient.

Shape memory polymers form polymeric material/s with the ability to sense and respond to external stimuli, e.g., temperature, pH, light, etc., in a predetermined way. Thermally induced shape memory polymers may exhibit a one-way shape memory effect due to their distinct thermal dynamics and polymer structures. Notably, this one-way memory effect differs from many shape memory alloys which can exhibit modulating shape memory effects due to the reversible nature of their grain microstructures, e.g., alternating between martensite and austenite repeatedly in response to repeated temperature changes.

In one example, shape memory polymers have polymer structures that can be considered as phase-segregated linear block copolymers having hard segments and soft segments. The hard segment, e.g., cross-linked, highly crystalline or semi-crystalline segment, acts as the frozen phase and the soft segment, e.g., amorphous or semi-crystalline segment, acts as the reversible phase. The reversible phase transformation of the soft segment is responsible for the shape memory effect. When the shape memory polymer is heated above the melting point (T(m)) or glass transition temperature (T(g)) of the hard segment, which is higher than the T(m) or T(g) of the soft segment, the material can be processed, e.g., molding, extrusion or the alike. This original shape can be memorized forming a remembered shape by cooling the shape memory polymer below the T(m) or T(g) of the hard segment. T(m) is hereinafter understood to refer to the melting temperature or melting temperature range of the polymers (or polymer segments) where the polymer crystal lattice structures are no longer stable and/or free rotation and movement of the polymers (or polymer segments) readily occurs. T(g) is hereinafter understood to refer to the glass transition temperature or glass transition temperature range, e.g., softening temperature, of the polymers (or polymer segments) where some free rotation and/or movement of the polymers (or polymer segments) can occur.

One method for forming a temporary shape is by deforming the material in the remembered shape at a temperature below the T(m) or T(g) of the hard segment but above the T(m) or T(g) of the soft segment and then cooling the material below the T(m) or T(g) of the soft segment to fix the deformed shape. The remembered or original shape is recovered by heating the shape memory polymer above the T(m) or T(g) of the soft segment, allowing at least some free rotation and/or movement of the soft segment for releasing the material from its temporary shape. Another method for setting the temporary shape involves the material in the remembered shape being deformed at a temperature lower than the T(m) or T(g) of the soft segment, resulting in stress and strain being absorbed by the soft segment. When the material is heated above the T(m) or T(g) of the soft segment, the stress and strains are relieved, e.g., via at least some free rotation and/or movement of the soft segment, and the material returns to its remembered shape. This is believed to be why the thermally induced shape memory polymers of the present invention have a one-way shape memory effect; they remember one permanent shape formed at the higher temperature, while many temporary shapes are possible at lower temperatures for which the systems do not have any memory because of the free rotation and/or movement of the soft segments.

The present invention employs polymeric material including shape memory polymers to form the elongated member or shaft of the catheter. In at least one embodiment, a first temporary shape of the elongated member has a relatively small outer diameter at about room temperature for insertion into the patient.

Once inside the patient, the elongated member is heated (e.g. passively via interaction with the patient's blood or actively via introduction of a heated saline solution or activation of an implanted heating element) where the elongated member self-configures to either its remembered shape or a second temporary shape for therapeutic treatment of the patient. In this configuration, the lumen of the catheter has a relatively larger flow area compared to the first temporary shape for fluid communication with the patient.

Applicants have found that even a small increase in the diameter of the lumen can significantly increase the volumetric flow rate through the catheter. For example, fluid flow through a circular cross-sectional flow area $(A=\pi r^2)$ of a catheter shaft can be described by Poiseuille's Law which is $Q=(8\mu\, L\Delta P)/(\pi\, r^4)$, where $\Delta P$ is the pressure drop, L is the length of the catheter shaft, $\mu$ is the dynamic viscosity, Q is the volumetric flow rate, r is the radius of the lumen of the catheter shaft which is equal to half its diameter $(r=\frac{1}{2}D)$, and $\pi$ is approximately 3.14. Since the radius (r) is to the fourth power, approximately a 0.005 inch increase in the diameter of about a 0.030 inch diameter lumen at a dynamic viscosity ($\mu$) of about 6.8 centipoise (cP) through approximately a 50 centimeter (cm) long catheter shaft at a pressure drop (ΔP) of about 25 pounds per square inch (psi) almost doubles the flow rate (Q) from about 0.45 milliliters per second (mL/sec) to about 0.84 mL/sec. In this example, the flow rate (Q) is increased substantially (e.g. about 86%) while the inner diameter of the lumen is increased only moderately (e.g. about 16%), which preferably results in only a moderate increase in the corresponding outer diameter (e.g. about 16%) of the catheter shaft such that the body vessel will not be occluded by the expanded catheter.

To remove the catheter, the elongated member may be further heated, e.g., via active heating or introducing a warm saline solution into the catheter, to return the elongated member to its final remembered state where the elongated member in at least one embodiment has a relatively small outer diameter. The interventionalist then removes the catheter preferably by pulling it out from the patient's body without difficultly.

Referring to FIGS. 1A-1D, a catheter in accordance with at least one embodiment of the present invention is provided. The catheter 10 is configured to be insertion into a patient's body and has an elongated member 12 with a proximal portion 14 extending to a distal portion 16. At least one lumen 18 is formed through the catheter 10. The lumen 18 extends through the proximal and distal portions 14 and 16.

The elongated member 12 is made from polymeric material which is preferably compliant and kink resistant, e.g., soft and elastomeric. In one example, the entire elongated member 12 is made from polymeric material or resin, e.g., by an extrusion process, pultrusion process or the alike. In another example, the elongated member 12 is made from at least two polymeric materials or resins, e.g., by co-extrusion (e.g. forming inner and outer layers), two-shot molding or the alike. For example, elongated member 12 may be co-extruded from two different polymeric resins where the first polymeric resin is extruded to form an inner layer and the second polymeric material is extruded to form an outer layer of the elongated member 12.

The polymeric material comprises shape memory polymers. Some examples of suitable polymers, which may be synthesized, formulated and/or compounded to have shape memory effects, are polyurethanes, polyester-urethanes, polyether-urethanes, polyesters, polyester-ethers, polyvinyl chlorides, silicones, and polyvinyl alcohols. The polymeric material may include one of these polymers, or at least two of these polymers may be blended or mixed together to preferably form a material with suitable shape memory properties.

In one embodiment, the polymeric material has a first phase transition temperature, e.g., T(m) or T(g) of the hard segments of the shape memory polymers, and a second phase transition temperature, e.g., T(m) or T(g) of the soft segments of the shape memory polymers. The second phase transition temperature is less than the first phase transition temperature but is greater than about room temperature. Room temperature varies but for the purposes of this application it is considered to be 22 degrees Celsius (° C.) +/−2° C. In one example, the first phase transition temperature is greater than about 37° C. and the second phase transition temperature is between about 22° C. and 37° C.

Figures 1A, 1B:
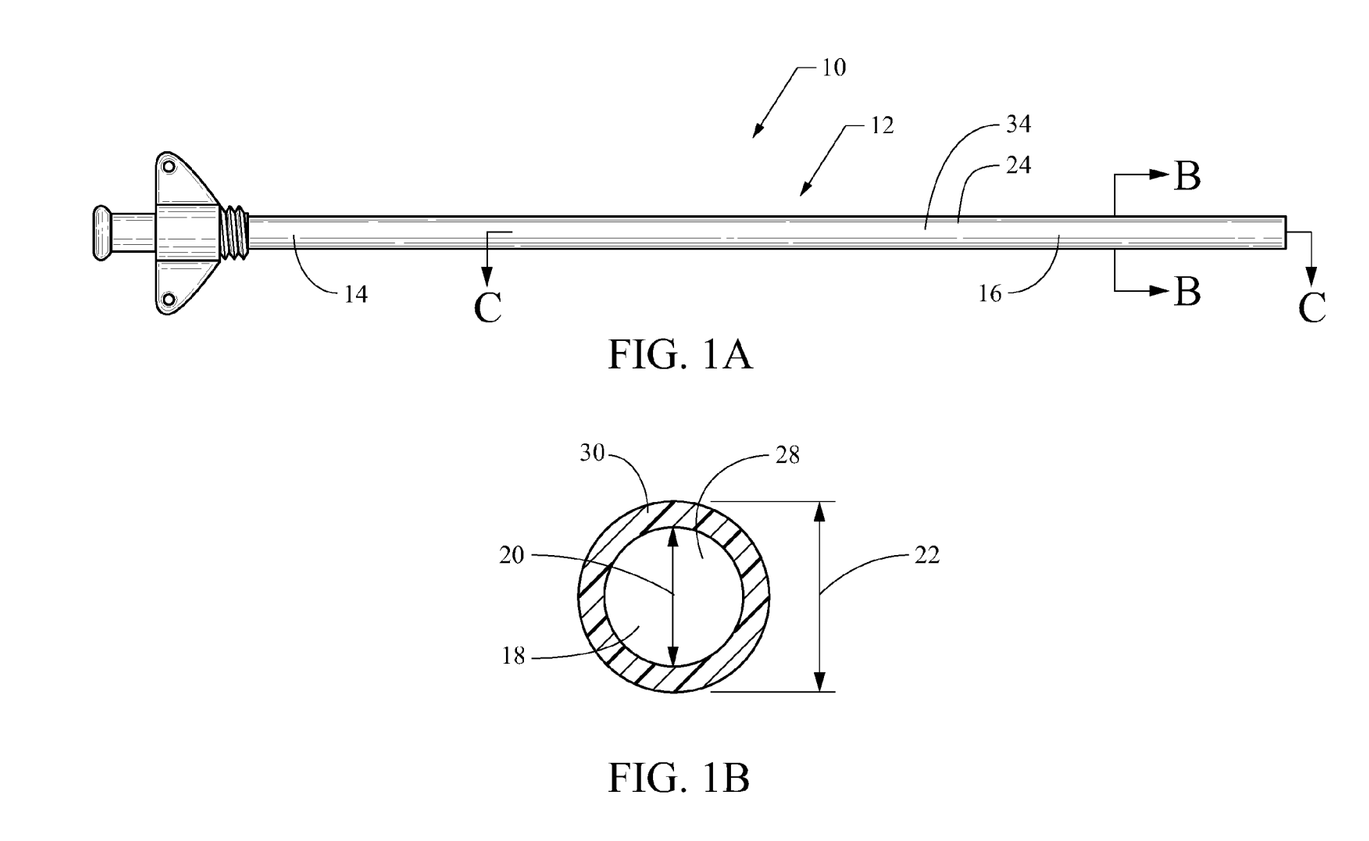
FIG. 1A is a catheter in accordance with an embodiment of the present invention.
FIG. 1B is an axial cross-section of the catheter depicted in FIG. 1A.
Figure 1C:
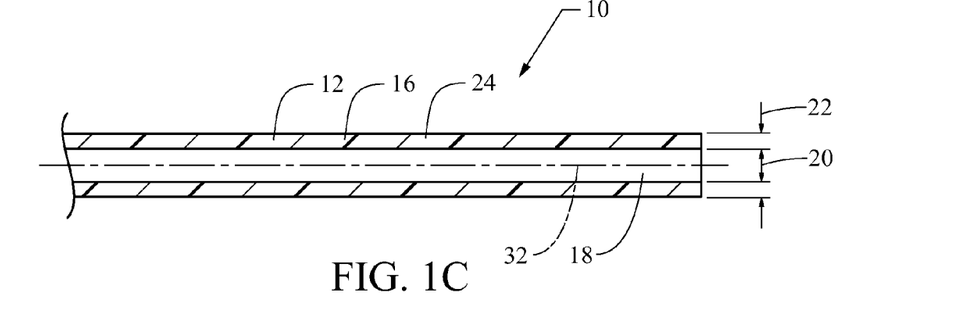
FIG. 1C is a longitudinal cross-section of the catheter depicted in FIG. 1A in accordance with an embodiment of the present invention.

As illustrated in FIG. 1C, the elongated member 12 has a first configuration 24 at about room temperature for insertion into the patient's body. That is, the first configuration 24 is a temporary shape. In this embodiment, the outer diameter 22 of the elongated member 12 is relatively small, e.g., between about 4 to 10 French. Correspondingly, the inner diameter 20 of the lumen 18 is also relatively small.

Figure 1D:
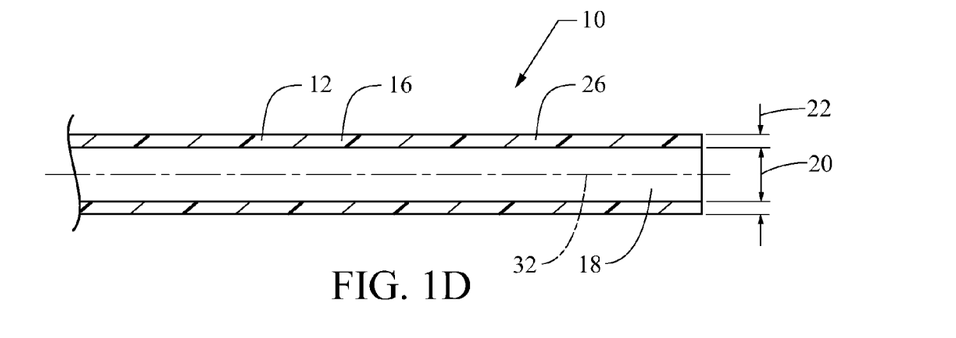
FIG. 1D is a longitudinal cross-section of the catheter depicted in FIG. 1A in accordance with one embodiment of the present invention.

In at least one embodiment of the present invention, the elongated member 12 self-configures to a second configuration 26 when at a temperature of at least the second phase transition temperature due to the shape memory properties of the polymeric material. That is, the second configuration 26 may be the remembered shape or it may be a second temporary shape of the catheter 10. At least a portion of the lumen 18 in the second configuration 26 has an increased flow area 28 relative to the portion of the lumen 18 in the first configuration 24 for enhancing fluid flow therethrough for therapeutic treatment of the patient.

Figure 1E:
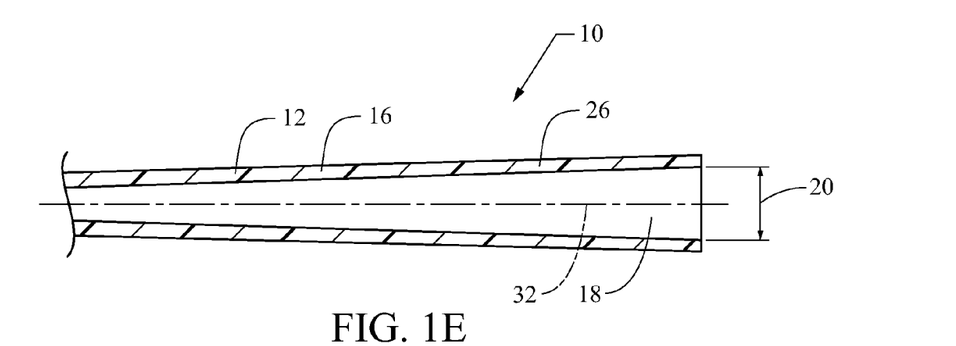
FIG. 1E is a longitudinal cross-section of the catheter depicted in FIG. 1A in accordance with another embodiment of the present invention.

In one example and with reference to FIGS. 1B-1D, the elongated member 12 has a cross-section 30 and a longitudinal axis 32. As illustrated, the elongated member 12 is defined by extrusion of the cross-section 30 along the longitudinal axis 32 where the cross-section 30 has an inner diameter 20 defining the flow area 28 (e.g. $A=\pi(D/2)^2$). The inner diameter 20 in the second configuration 26 is greater than in the first configuration 24 and is substantially constant along a length of the longitudinal axis 32 to increase the flow area 28 of at least the distal portion 16 of the elongated member 12. Alternatively and as illustrated in FIG. 1E, the inner diameter 20 of the lumen 18 may be variable and configured to flare distally along a length of the longitudinal axis 32 to increase the flow area 28. Other suitable catheter-lumen configurations may also be employed which preferably enhance the flow area 28 relative to the flow area 28 in the first configuration 24.

In one embodiment, the polymeric material includes a second plurality of polymers which are mixed or blended together with the first plurality of shape memory polymers. The second plurality of polymers may or may not include shape memory polymers but they have a different phase transition temperature, i.e., third phase transition temperature (e.g. transition temperature of corresponding soft segments of a second plurality of shape memory polymers), than the first plurality of shape memory polymers. The third phase transition temperature is greater than the first phase transition temperature. In one example, the third phase transition temperature is greater than about 42° C. and the first phase transition temperature is between about 37° C. and 42° C.

In this embodiment, the elongated member 12 has a third configuration 34, which may be the same or similar to the first configuration 24 illustrated in FIG. 1C, for removal from the patient's body. In particular, elongated member 12 self-configures from the second configuration 26 to the third configuration 34 at a temperature of at least the first phase transition temperature. The outer dimension of at least the distal portion 16 of elongated member 12 is less in the third configuration 34 than in the second configuration 26. As illustrated for example, the outer diameter 22 in the third configuration 34 is less than the outer diameter 22 in the second configuration 26, and is substantially constant along a length of the longitudinal axis 32.

In one embodiment, the various shape memory configurations (e.g. remembered and temporary shapes) of the elongated member 12 may be established as follows: The third configuration 34 is defined by a first narrowed outer diameter shape of elongated member 12 while being cooled through the third phase transition temperature. The second configuration 26 is defined by deforming the third configuration 34 (e.g. via expanding the lumen 18) while either being at a temperature below the first phase transition temperature or being cooled through the first phase transition temperature. The first configuration 24 is defined by deforming the second configuration (via narrowing the outer diameter 22) while either being at a temperature below the second phase transition temperature or being cooled through the second phase transition temperature.

Figure 2A:
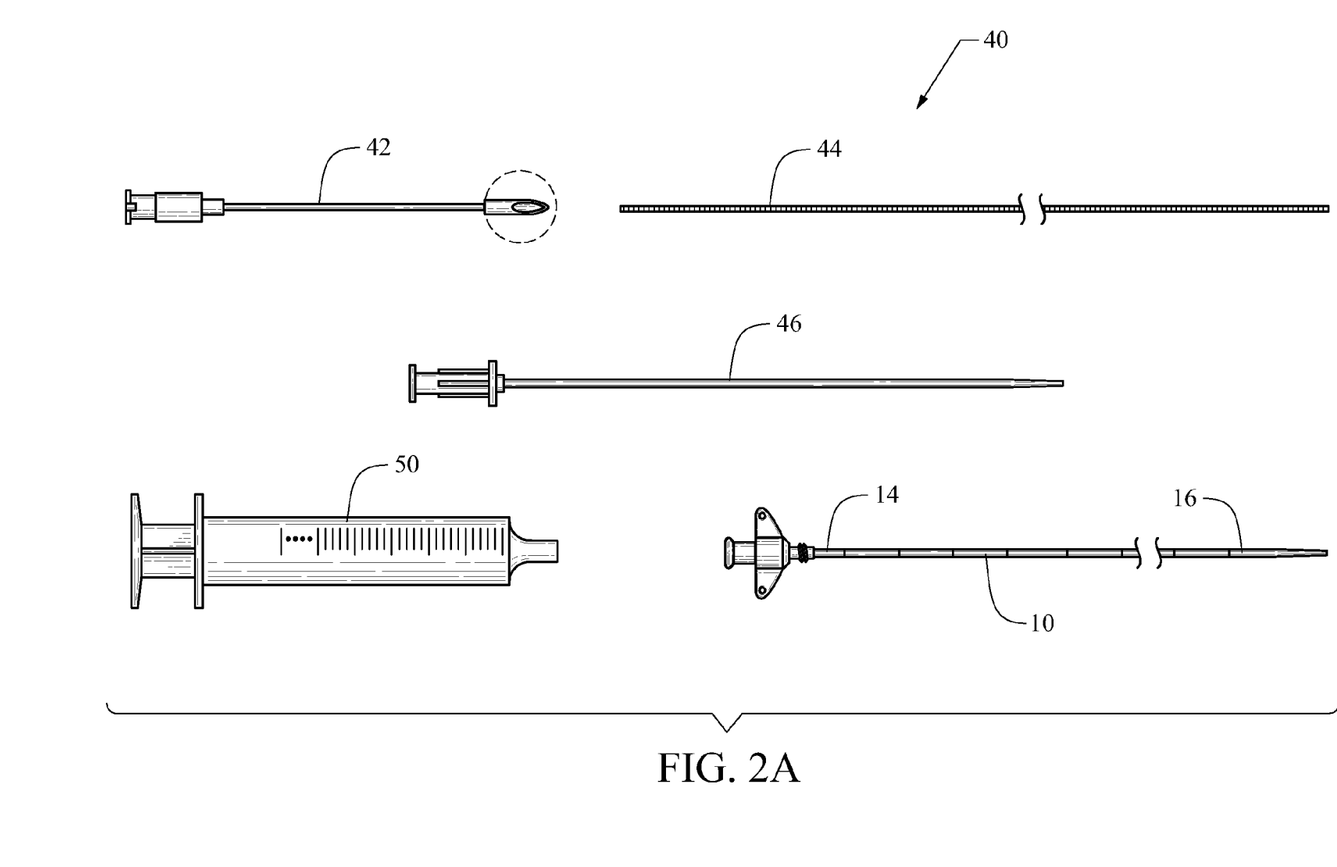
FIG. 2A is an exploded view of a catheterization kit in accordance with an embodiment of the present invention.
Figure 2B:
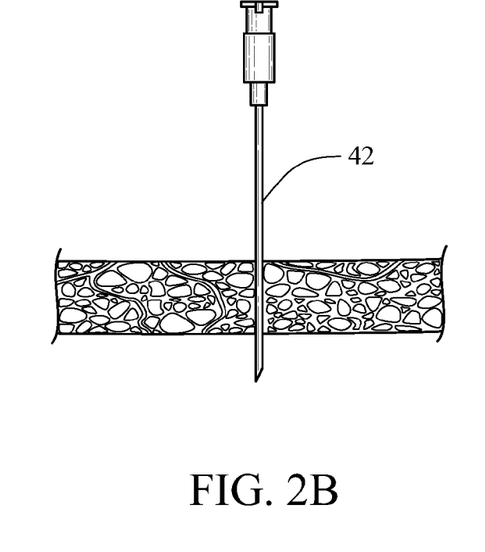
FIG. 2B is a needle inserted into a patient's body in accordance with one embodiment of the present invention.
Figure 2C:
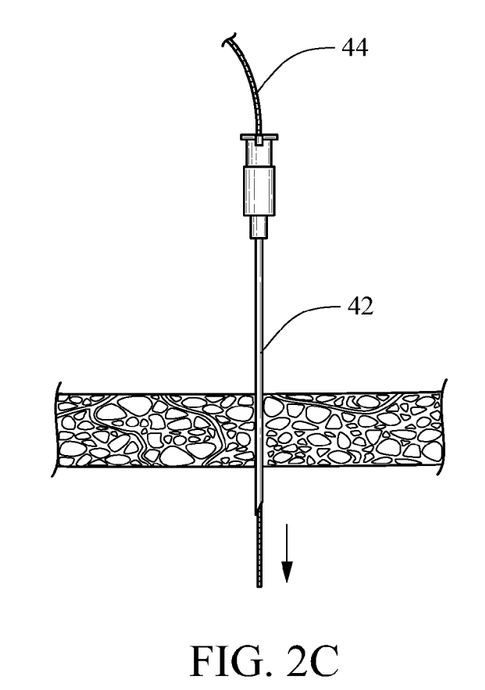
FIG. 2C is a wire guide being introduced into a patient's body in accordance with an embodiment of the present invention.
Figure 2D:
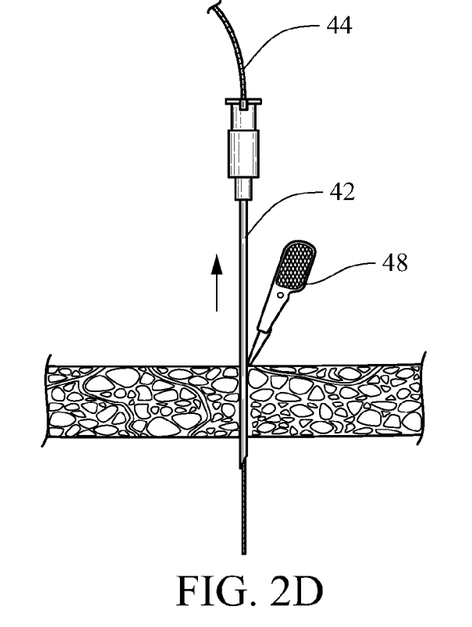
FIG. 2D is an example of an entry point into a patient's body being expanded in accordance with one embodiment of the present invention.

Referring to FIGS. 2A-2F, at least one embodiment of a catheterization kit is provided. As illustrated in FIG. 2A, the kit 40 includes a needle 42, a wire guide 44 and the catheter 10 as discussed in the foregoing paragraphs. The needle 42 is for percutaneously introducing the wire guide 44 into the patient's body (see FIGS. 2B-2C) through an access site and the wire guide 44 is for providing the catheter 10 a path for insertion into the patient's body (see FIG. 2F), such as for example, using the well-known Seldinger technique. A cutting device 48 may also be used to expand the access site (see FIG. 2D).

Figure 2E:
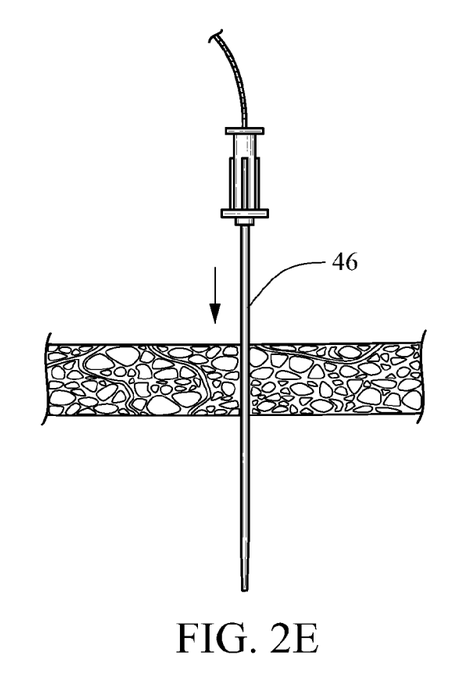
FIG. 2E is a dilator being introduced into a patient's body in accordance with one embodiment of the present invention.
Figure 2F:
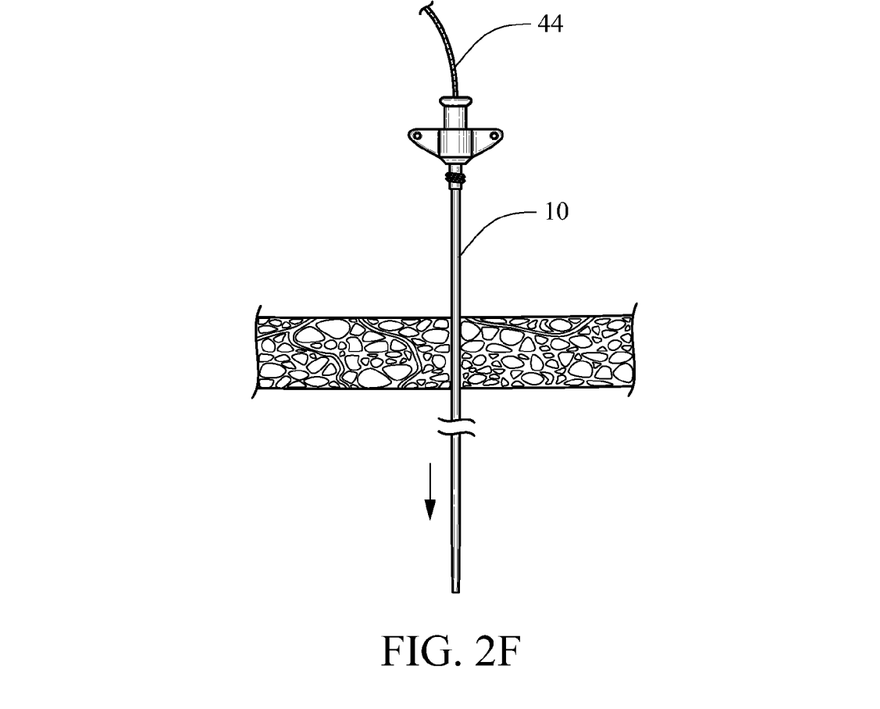
FIG. 2F is a catheter being introduced into a patient's body in accordance with an embodiment of the present invention.

The kit 40 may also include a dilator 46 configured to be advanced over the wire guide 44. The dilator 46 is used for dilating at least a portion of the path to facilitate inserting the catheter 10 into the patient's body (see FIGS. 2A and 2E-2F). A syringe 50 may be part of the kit 40 for administering therapeutic treatment and is configured to interface with a proximal portion 14 of the catheter 10 for fluid communication with the lumen 18.

Figure 3:
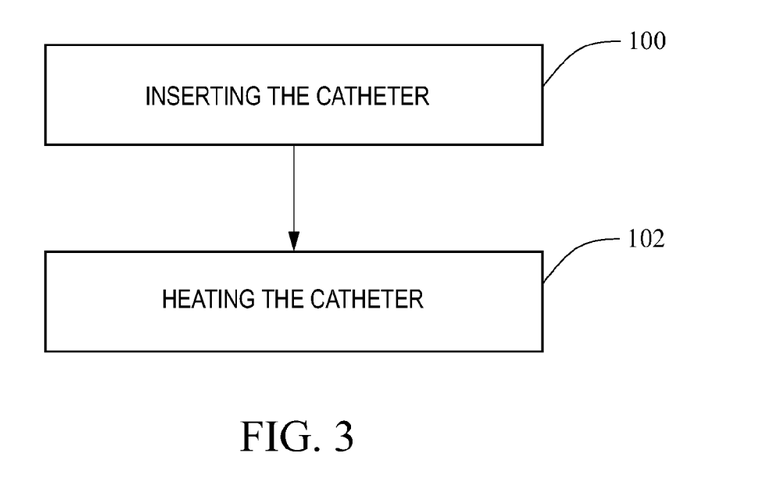
FIG. 3 is a flow chart of a method for catheterizing a patient's body in accordance with one example of the present invention.

Referring to FIG. 3, a method for catheterizing a patient for therapeutic treatment thereof in accordance with an example of the present invention is provided. The method comprises inserting an elongated member of a catheter at 100 into the patient's body. The elongated member is formed of polymeric material including shape memory polymers having a first phase transition temperature and a second phase transition temperature that is less than the first phase transition temperature but is greater than about room temperature. The elongated member is at about room temperature in a first configuration.

The elongated member is heated at 102 to a first temperature of at least a second phase transition temperature where the elongated member self-configures to a second configuration. At least a portion of a lumen formed through the elongated member has a larger flow area in the second configuration than in the first configuration.

As a person skilled in the art will readily appreciate, the above description is meant as an illustration of the implementation of the principles of the invention. This description is not intended to limit the scope or application of this invention in that the invention is susceptible to modification, variation, and change, without departing from the spirit of this invention as defined in the following claims.

What we claim is:

1. A catheter for insertion into a patient's body, the catheter comprising:
an elongated member having a proximal portion extending to a distal portion and a lumen formed therethrough, the elongated member formed of polymeric material including shape memory polymers having a first phase transition temperature and a second phase transition temperature that is less than the first phase transition temperature but greater than about room temperature, the elongated member having a first configuration at about room temperature for insertion into the patient's body and self-configures to a second configuration at a first temperature of at least the second phase transition temperature for fluid communication with the patient's body, at least a portion of the lumen having a larger flow area in the second configuration than in the first configuration, and a third configuration for removal from the patient's body and self-configures from the second configuration to the third configuration at a second temperature of at least the first phase transition temperature, the distal portion of the elongated member having an outer dimension that is less in the third configuration than in the second configuration.

2. The catheter according to claim 1 wherein the portion of the lumen with the larger flow area in the second configuration is formed through the distal portion of the elongated member.

3. The catheter according to claim 1 wherein the first phase transition temperature is greater than about 37° C. and the second phase transition temperature is between about 22° C. and 37° C.

4. The catheter according to claim 1 wherein the elongated member has a cross-section and a longitudinal axis, the elongated member is defined by extrusion of the cross-section along the longitudinal axis, the cross-section having an inner diameter defining the flow area, the inner diameter in the second configuration is greater than in the first configuration and is substantially constant along the longitudinal axis.

5. The catheter according to claim 1 wherein the elongated member has a cross-section and a longitudinal axis, the elongated member is defined by extrusion of the cross-section along the longitudinal axis, the cross-section having an inner diameter defining the flow area, the inner diameter in the second configuration is variable and is configured to flare distally along a length of the longitudinal axis to increase the flow area.

6. The catheter according to claim 1 wherein the elongated member has a longitudinal axis and a cross-section with an outer diameter, the elongated member is defined by extrusion of the cross-section along the longitudinal axis, the outer diameter in the third configuration is less than in the second configuration and is substantially constant along a length of the longitudinal axis.

7. The catheter according to claim 1 wherein the polymeric material has a third phase transition temperature that is greater than the first phase transition temperature, and the third configuration is defined by a first shape of the elongated member while being cooled through the third phase transition temperature, the second configuration is defined by deforming the third configuration while one of being at a temperature below the first phase transition temperature and being cooled through the first phase transition temperature, and the first configuration is defined by deforming the second configuration while one of being at a temperature below the second phase transition temperature and being cooled through the second phase transition temperature.

8. The catheter according to claim 7 wherein the third phase transition temperature is greater than about 42° C. and the first phase transition temperature is between about 37° C. and 42° C.

9. The catheter according to claim 7 wherein the elongated member has a co-extruded inner layer disposed about the lumen and a co-extruded outer layer that is disposed about the co-extruded inner layer, the polymer material including first shape memory polymers and second shape memory polymers, the first shape memory polymers are associated with at least one of the first and second phase transition temperatures, the second shape memory polymers are associated with the third phase transition temperature, and wherein one of the first and second shape memory polymers forms the co-extruded inner layer and the other of the first and second shape memory polymers forms the co-extruded outer layer.

10. A catheterization kit comprising:
a catheter for insertion into a patient's body, the catheter including:
an elongated member having a proximal portion extending to a distal portion and a lumen formed therethrough, the elongated member formed of polymeric material including shape memory polymers having a first phase transition temperature and a second phase transition temperature that is less than the first phase transition temperature but greater than about room temperature, the elongated member having a first configuration at about room temperature for insertion into the patient's body and self-configures to a second configuration at a first temperature of at least the second phase transition temperature for fluid communication with the patient's body, at least a portion of the lumen having a larger flow area in the second configuration than in the first configuration, and wherein the elongated member has a third configuration for removal from the patient's body and self-configures from the second configuration to the third configuration at a second temperature of at least the first phase transition temperature, the distal portion of the elongated member having an outer dimension that is less in the third configuration than in the second configuration;

a wire guide for providing the catheter a path during insertion into the patient's body; and a needle for introducing the wire guide into the patient's body.

11. The kit according to claim 10 further comprising at least one of a dilator and a syringe, the dilator is configured to be advanced over the wire guide for dilating at least a portion of the path to facilitate inserting the catheter into the patient's body, the syringe is configured to interface with the proximal portion of the elongated member for fluid communication with the lumen.

12. The kit according to claim 10 wherein the first phase transition temperature is greater than about 37° C. and the second phase transition temperature is between about 22° C. and 37° C.

13. The kit according to claim 10 wherein the elongated member has a longitudinal axis and a cross-section with an outer diameter, the elongated member is defined by extrusion of the cross-section along the longitudinal axis, the outer diameter in the third configuration is less than in the second configuration and is substantially constant along a length of the longitudinal axis.

* * * * *